United States Patent [19]

Takahashi et al.

[11] Patent Number: 4,859,774

[45] Date of Patent: Aug. 22, 1989

[54] FLOWABLE TRIETHYLENEDIAMINE

[75] Inventors: Akio Takahashi, Macungie; Robert G. Petrella, Allentown; Joel Schwartz, Whitehall, all of Pa.

[73] Assignee: Air Products and Chemicals Inc., Allentown, Pa.

[21] Appl. No.: 181,615

[22] Filed: Apr. 14, 1988

Related U.S. Application Data

[63] Continuation of Ser. No. 747,621, Jun. 21, 1985, abandoned.

[51] Int. Cl.$^4$ ............................................. C07D 471/08
[52] U.S. Cl. ..................................... 544/251; 252/384
[58] Field of Search ......................... 544/351; 252/382

[56] References Cited

U.S. PATENT DOCUMENTS

| | | | |
|---|---|---|---|
| 1,832,416 | 11/1931 | O'Brien | 252/384 |
| 1,885,905 | 11/1932 | Frost, Jr. | 252/384 |
| 1,989,752 | 2/1935 | Logue | 252/384 |
| 2,288,410 | 6/1942 | Lippman, Jr. | 252/384 |
| 2,370,011 | 2/1945 | Comstock | 252/384 |
| 2,372,402 | 3/1945 | Stokes | 252/384 |
| 2,539,012 | 1/1951 | Diamond | 252/384 |
| 2,557,155 | 6/1951 | Strashun | 252/384 |
| 2,589,330 | 3/1952 | Bradford | 252/384 |
| 3,305,491 | 2/1967 | Oster | 252/384 |
| 3,879,478 | 4/1975 | Chandler | 252/384 |
| 4,027,067 | 5/1977 | Wagner | 525/342 |
| 4,461,864 | 7/1984 | Flores | 524/300 |

FOREIGN PATENT DOCUMENTS 658160 4/1965 Belgium .

OTHER PUBLICATIONS

Kurata, II, Chem Abs 79, 17500s.
Horak, Chem Abs 102, 114612(f).
Derwent for Japanese 1879/62.
C F de r, Chem Abs 67, 44636 (1967).
Mitsui, Chem Abs 98, 216963 (1982).
Kurata T., Chem Abs 89, 5349t.

*Primary Examiner*—Mark L. Berch
*Attorney, Agent, or Firm*—Michael Leach; William F. Marsh; James C. Simmons

[57] ABSTRACT

The flowability of stored triethylenediamine is improved by admixing with a flow promoting amount of a salt, amide or ester derivative of a $C_8$–$C_{22}$ fatty acid. Especially suitable flow promoting additives for triethylenediamine are sales of stearic acid.

2 Claims, No Drawings

FLOWABLE TRIETHYLENEDIAMINE

This is a continuation of application Ser. No. 06/747,621 filed 21 June 1985, abandoned.

TECHNICAL FIELD

The invention relates to triethylenediamine crystal and, more particularly, relates to powdery triethylenediamine containing flow control additives.

BACKGROUND OF THE INVENTION

Triethylenediamine (TEDA), also known as 1,4-diazabicyclo(2.2.2)octane, is well known in the commercial market as a catalyst or cocatalyst in the production of polyurethane plastics, elastomers and foams. A number of methods are known in the art for preparing and isolating this compound as a product of commercially acceptable purity.

The production of TEDA may employ as a starting material an alkylene polyamine, mono- or bis-hydroxyethyl piperazine, N-aminoethyl piperazine, or alkanolamines alone or in mixture with ethylenediamine.

Typically, the TEDA is isolated from the reaction mixture as a white crystalline hygroscopic product containing a small amount of by-product amine compounds. The TEDA product is generally placed on the market for commercial users in drums of about 25 kg capacity.

With improved purification the synthesized TEDA product is recovered having less than about 500 ppm by-product organic amine impurities. It was found, however, that the purified commercial powdery crystalline TEDA product of this desired low content of organic amine impurities, when stored in commercial size drums for even short periods, particularly in a moderately warm environment, tended to develop a caking, or blocking, problem. This bulk aggregation of the powdery crystals is believed the result of two factors, namely (a) sublimation and recrystallization of the TEDA molecules forming a bridge between adjacent particles and (b) hygroscopicity which also results in agglomeration of adjacent particles. Thus the stored powdery product becomes very difficult to remove from the drum by pouring or scooping.

Japanese patent publication No. 82-203039 of Toya Soda Kogyo Co., Ltd. discloses non-solidifying triethylenediamine compositions comprising 0.01-2 parts by weight silica per 100 parts by weight triethylenediamine crystals. The bulk density of the silica should be less than 200 g/l.

U.S. Pat. No. 4,345,079 discloses a scoopable triethylenediamine containing a minor amount of an additive in liquid form which is a polyethylene glycol, a glycol ester, a glycol ether or an amino alcohol. Carbowax 400 polyethylene glycol was the preferred additive.

SUMMARY OF THE INVENTION

According to the present invention the flowability of triethylenediamine can be improved when a flow promoting amount of certain additives are admixed with the TEDA powder. The materials which are flow improving additives according to the invention are the salt, amide or ester derivative of a $C_8$-$C_{22}$ fatty acid.

TEDA compositions containing additives according to the invention remain as a flowable powder for a longer period and are much easier to render free flowing than TEDA product compositions according to the prior art.

DETAILED DESCRIPTION OF THE INVENTION

As flow promoting additives, the fatty acid derivatives may be admixed with the TEDA powder in any manner effective to obtain good dispersion throughout the mass. The admixing may be performed at a temperature ranging from ambient up to the melting point of the TEDA powder. The preferred additives are those which do not adversely affect the appearance or performance of the TEDA or blends of TEDA, such as aqueous solutions or mixtures with dipropylene glycol or dimethylethanolamine in catalyzing urethane and isocyanurate formation.

A flow promoting amount of the fatty acid derivatives are mixed with the TEDA powder, such as 0.01-1 parts of the fatty acid derivative per 100 parts of TEDA. While a degree of improvement in flowability is obtained when about 0.01% of the additive is used, such lower levels have not been found to afford the desired flowability of the TEDA for sufficiently long storage periods at warmer temperatures. At greater than 1 part/100 parts TEDA no additional advantage is obtained.

Although the fatty acid derivatives are relatively water insoluble, this does not, however, present a problem when the TEDA is employed in formulations in which it is dissolved in water, for example in the production of water-blow flexible polyurethane foams, because the actual use level is so low water solubility may be achieved. Water-solubility is not required where the TEDA is used as catalyst in non-aqueous urethane formulations, isocyanate polymerization or the like provided that the additive is sufficiently soluble in the polyol or other solvent or component of the formulations with which TEDA is to be mixed.

The additives according to the invention are the salt, amide or ester derivative of $C_8$-$C_{22}$ fatty acids, preferably fatty acids containing 12-18 carbon atoms. The fatty acids may be saturated in that they comprise long hydrocarbon chains containing no carbon-carbon double bonds or they may be unsaturated fatty acids containing one or more carbon-carbon multiple bonds. Among the fatty acids that are suitable for making the derivatives useful in the invention, there may be included caprylic, capric, myristic, palmitic, stearic, oleic, linoleic, and linolenic acids.

The salt, amide, or ester derivatives may be formed by any of the condensation reactions well known in the art such as reacting the fatty acid with the metal hydroxide, carbonate, bicarbonate or alcoholate; reacting the appropriate amine, or alcohol with the fatty acid, fatty acid halide or fatty acid ester. Many of the suitable fatty acid derivatives are commercially available.

Suitable metal salts of the fatty acids comprise as the metal component a Group IA metal such as lithium, sodium, or potassium; a Group IIA metal such as magnesium or calcium; or a Group IIIA metal such as aluminum.

The amide moiety of the fatty acid amide additives may be substituted or unsubstituted. The substituted amide moiety can be mono- or di-N-substituted with $C_1$-$C_8$ alkyl groups such as methyl, ethyl, 2-ethyl hexyl and the like.

The ester derivatives of the fatty acids would include the esters of $C_1$-$C_{18}$ branched or unbranched alkyl alcohols, such as methyl, ethyl, isopropyl, 2-ethyl hexyl and the like, as well as the diesters of polyethylene glycols of a molecular weight in the range of about 200 to about 2000.

In the following examples the flowability of TEDA was tested and rated as follows:

TEDA containing the indicated amount of a flow promoting additive was mixed in a Hobart mixer at speed #1 (139 gyrations/min.) at the specified heating mantle temperature for the specified time.

One pound of treated TEDA was placed in a 1 quart glass jar with a large mouth, capped tightly with a plastic cap and maintained at a selected temperature. Periodically, the jar was uncapped and a screwdriver with a shaft of ⅜″×¼″ thickness and 8″ length was manually driven through the TEDA in the jar. The flowability was rated by the magnitude of the force required to get the screwdriver through the TEDA mass as follows:

Poor—The screwdriver could not get through to the bottom of the jar. The entire TEDA mass was caked and difficult to break up into a powder.

Good—The screwdriver got through to the bottom of the jar. The TEDA mass was caked but could be broken up to a lump and then to a powder with some effort.

Excellent—The screwdrive got through with very little force. The entire TEDA mass broke into free flowing powder.

EXAMPLE 1

Various additives were subjected to a prescreening test to determine their suitability for improving flowability of plant produced TEDA having a content of by-product amine impurities in the range of about 100–500 ppm. The designated additives were incorporated in the respective amounts set forth in Table I with 900 g of TEDA. After mixing at the indicated temperature for 0.5 hours the product mixture was stored in two jars, one kept at room temperature for 16 hours and the other at 120° F. (49° C.) for one week.

| RUN | FLOW ADDIT (g) | TEDA (g) | MIXING TREATMENT (°F.) | FLOWABILITY 16 hr/RT | FLOWABILITY 1 wk./120° F. |
|---|---|---|---|---|---|
| 1 | | untreated | | poor | poor |
| 2 | | Toya Soda[g] | | very good | poor |
| 3 | Carbowax ® 400[a] (9) | 900 | RT | fair | poor |
| 4 | Hi Sil 233[b] (0.9) | 900 | RT | good | poor |
| 5 | Polypropylene Glycol[c] (4.5) | 900 | RT | fair | fair |
| 6 | Ca—Stearate (0.9) | 900 | RT | excellent | excellent |
| 7 | Polyethylene Glycol[d] (4.5) | 900 | 250–300 | good | poor |
| 8 | Polyethylene Glycol Monomethyl Ether[e] (4.5) | 900 | 250–300 | good | fair |
| 9 | Polyethylene Glycol Distearate[f] (4.5) | 900 | 250–300 | good | good/very good |
| 10 | Na—Stearate (0.9) | 900 | RT | very good/excellent | excellent |
| 11 | Al—Stearate (0.9) | 900 | RT | very good/excellent | excellent |
| 12 | DMAD[h] (2.25) | 900 | RT | very good | very good |
| 13 | DMAD (0.9) | 900 | RT | very good/good | good |
| 14 | 2-Ethylhexyl Stearate (2.25) | 900 | RT | very good/good | very good |
| 15 | 2-Ethylhexyl Stearate (0.9) | 900 | RT | very good/good | fair |

[a]Polyethylene glycol (400 molecular weight) marketed by Union Carbide
[b]A colloidal silica marketed by PPG Industries, Inc.
[c]4,000 molecular weight
[d]18,000 molecular weight
[e]1,900 molecular weight
[f]1,200 molecular weight
[g]TEDA marketed by Toya Soda Kogyo Co., Ltd. believed to contain silica
[h]A dimethylamide of fatty acid marketed by Buckman Labs It can be seen from Table I that untreated TEDA powder (Run 1) demonstrated poor flowability after 16 hours at room temperature and one week at 120° F. The Toya Soda TEDA product which is believed to contain silica as a flow aid (Run 2) showed very good flowability after the 16 hour/room temperature storage but showed poor flowability after one week at 120° F. Run 4 which used a colloidal silica additive gave similar performance.

Polypropylene glycol (Run 5) and polyethylene glycol (Run 7) present at a level of 4.5 grams per 900 grams TEDA showed fair and good flowability, respectively, at 16 hours/room temperature and were only rated fair and poor, respectively, at one week/120° F. The monomethyl ether of polyethylene glycol (Run 8) while rated good during the room temperature test deteriorated to a fair rating over the longer test at higher temperature.

The salts of stearic acid, namely the calcium salt (Run 6), the sodium salt (Run 10) and the aluminum salt (Run 11) were all rated very good/excellent when tested after 16 hours/room temperature and, surprisingly, were all rated excellent after a week at the elevated temperature. This is in contrast to the prior art additives (Runs 3–5, 7 and 8) which appeared to lose performance over the extended time period and elevated temperatures.

The polyethylene glycol and 2-ethylhexyl esters of stearic acid (Runs 9 and 14) at 0.5 and 0.25 wt% were at least good when tested after 16 hours/room temperature and showed additional slight flowability improvement at the one week/120° F. testing. Surprisingly, the TEDA-containing 0.1 wt% 2-ethylhexyl stearate (Run 15) showed poor results after the extended/higher temperature testing. This result seems to indicate that at least about a 0.2 wt% level of 2-ethylhexyl stearate should be used.

The use of an amide derivative of a fatty acid is demonstrated in Runs 12 and 13 which employed the dimethyl amide of a fatty acid at 0.25 and 0.1 wt% levels, respectively. The flowability test results at both test conditions for Runs 12 and 13 were very good for the higher additive level and at least good for the lower content level. These runs also seem to indicate that at least 0.2 wt% of the dimethyl amide of a fatty acid should be used as a flow additive.

EXAMPLE 2

This Example presents flowability results comparing stearate salt additives versus the polyethylene glycol and silica prior art additives. The indicated amount of additive was incorporated for 10 parts powdery TEDA crystal by mixing for 0.5 hr. at room temperature in the Hobart mixer at 139 gyrations per minute. The flow additive treated TEDA was then tested for flowability at three different conditions, namely room temperature for 16–72 hours, 120° F. for 7 days and 120° F. for 14 days.

It can be seen from Table II that Runs 16–18 using the prior art treated TEDA all demonstrated significant deterioration in the flowability on exposure to elevated temperatures (120° F.) for extended periods (1 and 2 weeks). In marked contrast, the sodium, aluminum and calcium salts of stearic acid all showed excellent flowability under the test conditions.

ability at room temperature/16–72 hours, 120° F./7 days and 120° F./14 days.

The data in Table III show that the polyethylene glycol distearate treated TEDA (Run 25) demonstrated good flowability after room temperature storage and very good flowability after storage at 120° F. for one and two weeks. Although the results were always good, if the mixture temperature is below the melting point of polyethylene glycol distearate, its effectiveness is diminished. The TEDA composition treated with 2-ethylhexyl stearate (Run 26) showed very good flowability at the room temperature testing but showed deteriorated flowability after storage for extended time at elevated temperatures. From this result and the data for Runs 14 and 15 in Table I, it appears that the performance of 2-ethylhexyl stearate is concentration dependent with about a 0.25 wt% level preferred. Both Runs 27 and 28 of TEDA treated with a fatty acid amide demonstrated flowability under the three test conditions vastly superior to the prior art treated TEDA compositions.

TABLE III

| RUN | FLOW ADDITIVE[a] (pbw) | MIXING TREATMENT °F. | FLOWABILITY RT/16–72 HRS | 120° F./7 DAYS | 120° F./14 DAYS |
|---|---|---|---|---|---|
| 23 | CARBOWAX 400 (1.0) | RT | FAIR | POOR | POOR |
| 24 | TOYO SODA TEDA (—) | — | VERY GOOD | POOR | VERY POOR |
| 25 | POLYETHYLENE GLYCOL DISTEARATE (0.5) | 250–300 | GOOD | VERY GOOD | VERY GOOD |
| 26 | 2-ETHYLHEXYL STEARATE (0.50) | RT | VERY GOOD | FAIR | POOR |
| 27 | DMAD[b] (0.50) | RT | VERY GOOD | EXCELLENT | EXCELLENT |
| 28 | DMAD (0.25) | RT | VERY GOOD | GOOD/ VERY GOOD | — |

[a]PART BY WEIGHT PER 100 PARTS TEDA
[b]A TINT OF YELLOW

STATEMENT OF INDUSTRIAL APPLICATION

The invention provides for improving the flowability of stored powdery TEDA crystals by the incorporation of a flow improving amount of a derivative of a fatty acid.

TABLE II

| RUN | FLOW ADDITIVE[a] (pbw) | MIXING TREATMENT °F. | FLOWABILITY RT/16–72 HRS | 120° F./7 DAYS | 120° F./14 DAYS |
|---|---|---|---|---|---|
| 16 | CARBOWAX 400 (1.0) | RT | FAIR | POOR | POOR |
| 17 | TOYO SODA TEDA (—) | — | VERY GOOD | POOR | VERY POOR |
| 18 | HI SIL 233 (0.1) | RT | GOOD | POOR | — |
| 19 | Na—STEARATE (0.1) | RT | EXCELLENT | EXCELLENT | EXCELLENT |
| 20 | Na—STEARATE (0.025) | RT | EXCELLENT | VERY GOOD/ EXCELLENT | VERY GOOD/ EXCELLENT |
| 21 | Al—STEARATE (0.1) | RT | EXCELLENT | EXCELLENT | — |
| 22 | Ca—STEARATE (0.1) | RT | EXCELLENT | EXCELLENT | — |

[a]PART BY WEIGHT PER 100 PARTS TEDA

EXAMPLE 3

In this Example TEDA treated with flow additives comprising esters and amides of fatty acids were compared to the prior art flowable TEDA compositions of Runs 23 and 24. Again the indicated amount of flow additive was incorporated per 100 parts of TEDA at 139 gyrations per minute in a Hobart mixer for 30 minutes at the indicated heating mantle temperature. The flow additive treated TEDA was then tested for flow-

We claim:

1. In a method for improving the flowability of triethylenediamine by admixing with a flow-promoting additive, the improvement which consists essentially of admixing sodium stearate with triethylenediamine at about 250 ppm.

2. A flowable composition of triethylenediamine which consists essentially of about 0.025 parts by weight sodium stearate per 100 parts triethylenediamine.

* * * * *